United States Patent [19]

Fried et al.

[11] 4,009,197

[45] * Feb. 22, 1977

[54] 2-(6-SUBSTITUTED-2'-NAPHTHYL) ACETIC ACID DERIVATIVES AND THE SALTS AND ESTERS THEREOF

[75] Inventors: John H. Fried; Ian T. Harrison, both of Palo Alto, Calif.

[73] Assignee: Syntex Corporation, Panama, Panama

[ * ] Notice: The portion of the term of this patent subsequent to Sept. 9, 1992, has been disclaimed.

[22] Filed: May 1, 1975

[21] Appl. No.: 573,483

Related U.S. Application Data

[63] Continuation of Ser. No. 372,028, June 21, 1973, Pat. No. 3,904,682, which is a continuation of Ser. No. 176,740, Aug. 31, 1971, abandoned, which is a continuation-in-part of Ser. Nos. 694,771, Dec. 7, 1967, abandoned, Ser. No. 810,013, March 24, 1969, abandoned, and Ser. No. 810,014, March 24, 1969, abandoned, said Ser. No. 810,013, and Ser. No. 810,014, each is a continuation-in-part of Ser. No. 694,771, , and Ser. No. 608,997, Jan. 13, 1967, abandoned, said Ser. No. 694,771, is a continuation-in-part of Ser. No. 608,997.

[52] U.S. Cl. .......................... 260/473 F; 260/520 D
[51] Int. Cl.$^2$ ........................................ C07G 69/76
[58] Field of Search ..................... 260/473 F, 520 D

[56] References Cited

UNITED STATES PATENTS

| | | | |
|---|---|---|---|
| 3,506,671 | 4/1970 | Kaiser et al. | 260/515 A |
| 3,663,584 | 5/1972 | Alvarez | 260/473 F |
| 3,681,432 | 8/1972 | Nelson | 260/473 F |

FOREIGN PATENTS OR APPLICATIONS

| | | |
|---|---|---|
| 2,013,641 | 10/1970 | Germany |
| 2,005,454 | 10/1970 | Germany |
| 6,771 | 5/1963 | Japan |
| 677,597 | 6/1968 | South Africa |

*Primary Examiner*—Paul J. Killos
*Attorney, Agent, or Firm*—Joseph I. Hirsch; William B. Walker

[57] ABSTRACT

2-(6'-Substituted-2'-naphthyl)acetic acid derivatives substituted at the 2-position of the acetic acid moiety with methyl, methylene or halomethylene and the salts and esters thereof have anti-inflammatory, analgesic and anti-pyretic activities.

11 Claims, No Drawings

2-(6-SUBSTITUTED-2'-NAPHTHYL) ACETIC ACID DERIVATIVES AND THE SALTS AND ESTERS THEREOF

This application is a continuation of application Ser. No. 372,028, filed June 21, 1973, now U.S. Pat. No. 3,904,682, which is a continuation of application Ser. No. 176,740, filed Aug. 31, 1971, now abandoned, which, in turn, is a continuation-in-part of application Ser. No. 694,771, filed Dec. 7, 1967, now abandoned, and application Ser. Nos. 810,013 and 810,014, both filed Mar. 24, 1969, both now abandoned, the aforesaid application Ser. Nos. 810,013 and 810,014 being, in turn, continuations-in-part of aforesaid application Ser. No. 694,771 and application Ser. No. 608,997, filed Jan. 13, 1967, now abandoned, and the aforesaid application Ser. No. 694,771 being a continuation-in-part of aforesaid application Ser. No. 608,997.

This invention relates to novel 2-(6'-substituted-2'-naphthyl)acetic acid derivatives and salts and esters thereof which are useful as anti-inflammatory, analgesic and anti-pyretic agents.

The compounds of this invention are the carboxylic acids and carboxylic acid esters represented by the following formula, and the pharmaceutically acceptable salts of the carboxylic acids represented by the following formula:

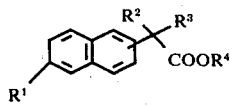

(I)

In the above formula, $R^1$ is alkyl having up to 6 carbon atoms, cycloalkyl having from 3 to 7 carbon atoms, alkoxymethyl having up to 7 carbon atoms, trifluoromethyl, vinyl, ethynyl, halo, (iodo, bromo, chloro or fluoro) alkoxy having up to 6 carbon atoms, difluoromethoxy, alkoxymethyloxy having up to 7 carbon atoms, alkylthiomethyloxy having up to 7 carbon atoms, alkylthio having up to 6 carbon atoms, alkoxymethylthio having up to 7 carbon atoms, alkylthiomethylthio having up to 7 carbon atoms, cyano, difluoromethylthio, phenyl or alkylsubstituted phenyl having up to 8 carbon atoms;

one of $R^2$ and $R^3$ is hydrogen, the other being methyl, ethyl or difluoromethyl or $R^2$ and $R^3$ together are methylene;

$R^4$ is hydrogen, alkyl having up to 22 carbon atoms, unsaturated alkyl having up to 22 carbon atoms, cycloalkyl having from 3 to 7 carbon atoms, cycloalkylmethyl having from 4 to 9 carbon atoms, 2-cycloalkylethyl having from 5 to 10 carbon atoms, 3-cyclopentylpropyl, 3-cyclohexylpropyl, benzyl, 2-phenylethyl or 3-phenylpropyl.

Preferably, the 6'-substituent (represented by $R^1$ in the above formula) is methyl, ethyl, isopropyl, cyclopropyl, trifluoromethyl, vinyl, ethynyl, fluoro, chloro, methoxy, ethoxy, methoxymethyloxy, difluoromethoxy, methylthio, ethylthio, methoxymethylthio, difluoromethylthio or phenyl; one of $R^2$ and $R^3$ is hydrogen and the other is methyl; and $R^4$ is hydrogen, methyl, ethyl, propyl, isopropyl, butyl, pentyl, isopentyl, hexyl, 2-hexyl, isohexyl, heptyl, isoheptyl, octyl, isooctyl, nonyl, isononyl, decyl, isodecyl, undecyl, dodecyl, tridecyl, tetradecyl, pentadecyl, hexadecyl, cyclopentyl or cyclohexyl.

The term "alkyl" refers to and includes branched and straight chain hydrocarbons. Typical alkyl groups include methyl, ethyl, propyl, isopropyl, butyl, tertiary butyl, neopentyl, isopentyl, hexyl, octyl, nonyl, isodecyl, 6-methyldecyl, tridecyl, isotetradecyl, pentadecyl, isohexadecyl, heptadecyl, eicosyl, docosyl, and the like. The term "unsaturated alkyl" refers to unsaturated hydrocarbon groups such as vinyl, allyl, propenyl, crotyl, isopropenyl, 2-propynyl, 1-propenyl, 2-butenyl, 1,3-butadienyl, 2-pentenyl, 2-penten-4-ynyl and the like.

The term "cycloalkyl" refers to cyclo hydrocarbon groups such as cyclopropyl, cyclobutyl, cyclopentyl, cyclohexyl and cycloheptyl.

The term "alkoxy" refers to straight or branched chain alkyl ether groups such as methoxy, ethoxy, 2-propoxy, butoxy, 3-pentoxy and the like.

The term "alkoxymethyloxy" refers to methyl ether groups substituted with one alkoxy group (defined above) such as methoxymethyloxy, ethoxymethyloxy, isopropoxymethyloxy and the like.

The term "alkylthio" refers to straight or branched chain alkylthio ether groups such as methylthio, ethylthio, propylthio, 2-propylthio, 2-butylthio, pentylthio, 3-hexylthio and the like.

The term "alkylthiomethyloxy" refers to methyl ether groups substituted with an alkylthio group (defined above) such as methylthiomethyloxy, 2-propylthiomethyloxy, pentylthiomethyloxy and the like.

The term "alkylthiomethylthio" as used herein denotes methylthio ether groups substituted with an alkylthio group such as methylthiomethylthio, ethylthiomethylthio and the like.

The term "alkoxymethylthio" refers to methylthio ether groups substituted with an alkoxy group such as methoxymethylthio, ethoxymethylthio, 2-propoxymethylthio and the like.

The term "aryl" refers to phenyl, or o-, m- and/or p-alkyl-substituted phenyl derivatives such as phenyl, o-tolyl, m-tolyl, p-tolyl, o-ethylphenyl, m-ethylphenyl, p-ethylphenyl, xylyl and the like.

The term "cycloalkylmethyl" refers to cycloalkyl substituted methyl groups such as cyclopropylmethyl, cyclobutylmethyl, cyclopentylmethyl, cyclohexylmethyl, cycloheptylmethyl, and the like. The term "2-cycloalkylethyl" refers to an ethyl group substituted at the 2-position with a cycloalkyl group such as 2-cyclopropylethyl, 2-cyclobutylethyl, 2-cyclopentylethyl, 2-cyclohexylethyl and 2-cycloheptylethyl.

The term "pharmaceutically acceptable salts" refers to salts prepared from pharmaceutically acceptable non-toxic bases including inorganic bases and organic bases. Salts derived from inorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglucamine, theobromine, purines, piperazine, piperidine, polyamine resins and the like.

When one of $R^2$ and $R^3$ is hydrogen and the other is methyl or difluoromethyl, the compounds of Formula I exist as pairs of enantiomorphs. Each enantiomorph or optical isomer and mixtures thereof are included within the present invention. The compounds of Formula I which exist as pairs of enantiomorphs can be administered as racemic mixtures or they can be administered as resolved enantiomorphs. In some instances, one enantiomorph exhibits greater anti-inflammatory, analgesic and/or anti-pyretic activity than the other corresponding enantiomorph.

The optical isomers can be resolved by conventional means, such as selective biological degradation or by the preparation of diastereo-isomer salts of the carboxylic acid with an optically active amine base such as cinchonidine and separating the diastereoisomers by fractional crystallization. The separated diastereoisomer salts are then acid cleaved to yield the respective optical isomers.

The compounds of this invention exhibit anti-inflammatory, analgesic and anti-pyretic activities. Accordingly, these compounds are useful in the treatment and elimination of inflammation such as inflammatory conditions of the muscular skeletal system, skeletal joints and other tissues. Accordingly, these compounds are useful in the treatment of conditions characterized by inflammation, such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

The preferred manner of administration is oral using a convenient daily dosage regimen which can be adjusted according to the degree of affliction. Generally, a daily dose of from 0.1 mg. to 20 mg. of the active compound per kilogram of body weight is used. Most conditions respond to treatment comprising a dosage level of the order of 1 mg. to 10 mg. per kilogram of body weight per day. For such oral administration, a pharmaceutically acceptable non-toxic composition is formed by the incorporation of any of the normally employed excipients. These compositions take the form of solutions, suspensions, tablets, pills, capsules, powders, sustained release formulations and the like. In addition, the compounds of this invention can be administered in conjunction with other medicinal agents depending upon the specific condition being treated.

The compounds of this invention can be prepared from known starting compounds. For example, one such method by which they can be prepared involves the reaction of a substituted naphthalene with acetyl chloride in nitrobenzene in the presence of about three molar equivalents of aluminum chloride to afford the corresponding 2-acetylnaphthalene derivative. The resulting derivative is heated with morpholine in the presence of sulfur at 150° C; the resulting product is refluxed with concentrated hydrochloric acid or alcoholic sodium hydroxide followed by acidification to furnish the corresponding 2'-naphthylacetic acid derivative.

The naphthalenes that are used in the above process can be illustrated by the following formula:

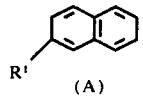

wherein $R^1$ is as defined above.

The naphthalenes of Formula A are known to the art. Moreover, they can be prepared by conventional means. For example, methoxybenzene is treated with succinic anhydride and aluminum chloride in a hydrocarbon solvent to afford 4-(4'-methoxyphenyl)-4-oxobutanoic acid. This is reduced by treatment with sodium borohydride and hydrogenolyzed by treating with palladium-on-charcoal catalyst and hydrogen to furnish 4-(4'-methoxyphenyl)-butanoic acid. The corresponding acid chloride can be prepared by treatment with thionyl chloride, and the acid chloride is treated with aluminum chloride to afford 7-methoxy-1-tetralone. The tetralone is reduced and hydrogenolyzed by the means described above to furnish 6-methoxytetralin which is dehydrogenated by treating with palladium-on-charcoal catalyst to afford 2-methoxynaphthalene. By utilizing methylbenzene in the above process, 7-methyl-1-tetralone (as an intermediate) and 2-methylnaphthalene is prepared.

2-Alkyl, 3-cycloalkyl, or 2-aryl substituted naphthalenes of Formula A wherein $R^1$ is alkyl or aryl can be prepared from 2-tetralone by treating the latter with an equivalent of an alkyl, cycloalkyl or aryl magnesium bromide in an ether to obtain the corresponding 2-alkyl-, 2-cycloalkyl-, or 2-aryl-3,4-dihydronaphthalene which is dehydrogenated by heating with palladium charcoal catalyst to afford the corresponding 2-alkyl, 2-cycloalkyl, or 2-arylnaphthalenes.

2-Vinylnaphthalenes are prepared by refluxing 2-ethylnaphthalene with a molar equivalent of N-bromosuccinimide in a halohydrocarbon solvent, such as chloroform, methylene chloride, dichloroethane, carbon tetrachloride, 1,4-dichlorobutane, chlorobenzene, chloroethane, chlorocyclohexane, dichlorobenzene, and the like. In light and in the presence of a trace amount of peroxide, such as benzoyl peroxide, t-butyl peroxide, peroxyacetic acid, and the like, to afford the corresponding 2-(1'-bromoethyl)naphthalene. The latter is dehydrobrominated by treating with lithium carbonate in dimethylformamide to afford 2-vinylnaphthalene.

2-Ethynylnaphthalene is prepared from 2-vinylnaphthalene by brominating the latter in a halohydrocarbon solvent and then dehydrobrominating the resulting 2-(1',2'-dibromoethyl)naphthalene by conventional means, such as by treatment with sodium amide in liquid ammonia, to furnish the 2-ethynylnaphthalene.

2-Cyclopropylnaphthalene is prepared from 2-vinylnaphthalene by refluxing in ether with diiodomethane in the presence of zinc:copper couple.

2-Cyclobutylnaphthalene is prepared from 2-naphthylmagnesium bromide by treating the latter with cyclobutanone to furnish 2-(1'-hydroxycyclobutyl)naphthalene, which is hydrogenolyzed with hydrogen in the presence of Raney nickel to furnish 2-cyclobutylnaphthalene.

2-Cyclopentylnaphthalene can be prepared by heating naphthalene with cyclopentyl benzenesulfonate. 2-Cyclohexylnaphthalene can be similarly prepared by employing cyclohexyl benzenesulfonate.

2-Acetylnaphthalene is prepared by treating 2-(1-bromoethyl)naphthalene, prepared as described above, with sodium acetate in acetic acid to afford 2-(1-acetoxyethyl)naphthalene which upon base hydrolysis furnishes the 2-(1-hydroxyethyl)naphthalene. The latter is oxidized with an equivalent of chromium trioxide in glacial acetic acid, or 8N sulfuric acid and acetone to furnish 2-acetylnaphthalene. 2-Carboxynaphthalene is prepared from 2-acetylnaphthalene by treating the latter with aqueous sodium hypochlorite. The 2-carboxynaphthalene is treated with diborane in an ether, such as diglyme (diethyleneglycol dimethyl ether), to yield 2-hydroxymethylnaphthalene.

The 2-hydroxymethyl group is etherified to form alkoxymethyl groups by conventional means employed to etherify primary hydroxy groups.

2-Formylnaphthalene is prepared from 2-hydroxymethylnaphthalene by treating the latter with manganese dioxide in a halohydrocarbon solvent.

2-Cyanonaphthalene is prepared by refluxing 2-formylnaphthalene with hydroxylamine hydrochloride and sodium acetate in ethanol to furnish the corresponding oxime which is refluxed with acetic anhydride in the presence of an acid catalyst to furnish 2-cyanonaphthalene.

Alternatively, the above substituents can be introduced on a naphthylacetic acid ester derivative by using an ethyl or vinyl substituted naphthylacetic acid ester derivative as a starting material.

Preferably, the trifluoromethyl, difluoromethoxy, difluoromethylthio, alkoxymethyloxy, alkoxymethylthio, alkylthiomethyloxy and alkylthiomethylthio groups are introduced on the 2-naphthylacetic acid derivatives as one of the final steps.

Another method or preparing the compounds of this invention employs substituted 1-tetralones and can be illustrated by the following reaction sequence:
wherein $R^{11}$ represents the groups represented by $R^1$ and additionally a hydroxy group.

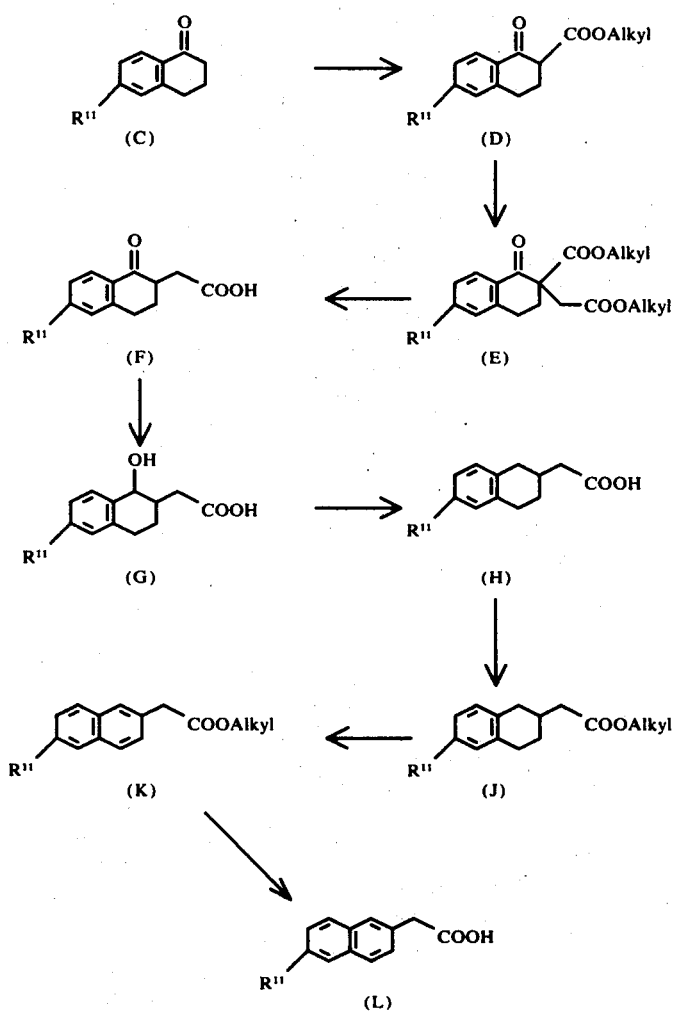

The 1-tetralones, the compounds of Formula C, are heated with two or more equivalents of a dialkyl carbonate, such as diethyl carbonate, in the presence of one or more equivalents of an alkali metal hydride, such as sodium hydride, potassium hydride, and the like, in a hydrocarbon solvent, such as hexane, cyclohexane, heptane, isooctane, benzene, toluene, xylene, and the like, to afford the corresponding alkoxy carbonyl compounds of Formula D. The latter are treated with an alkali metal hydride in a hydrocarbon solvent; the resulting products are treated with an α-haloacetic acid ester such as ethyl α-bromoacetate, methyl α-iodoacetate, and the like, to furnish the corresponding 2-alkoxycarbonyl-2-(alkoxycarbonylmethyl)-1-tetralones of Formula E. The latter are hydrolyzed with an acid, such as hydrochloric acid, sulfuric acid, p-toluenesulfonic acid, and the like to obtain the 2-(carboxymethyl) compounds of Formula F. The latter are reduced with a reducing agent, such as sodium borohydride, lithium borohydride; or with one equivalent of hydrogen in the presence of Adam's catalyst, and the like, to afford the hydroxy compounds of Formula G which are hydrogenolyzed by treatment with an equivalent amount of hydrogen in the presence of a hydrogenation catalyst, such as platinum, palladium, and the like, to furnish the corresponding 1,2,3,4-tetrahydro-2-naphthylacetic acid derivatives of Formula H. The compounds of Formula H are esterified by conventional means, such as the means described above, to afford the compounds of Formula J; these are dehydrogenated by heating with palladium-on-charcoal catalyst at temperatures of 180° C and higher to furnish the corresponding 2-naphthylacetic acid ester derivatives, the compounds of Formula K. The latter compounds are hydrolyzed to the corresponding 2-naphthylacetic acid derivatives, the compounds of Formula L, by conventional hydrolysis, such as by treatment with an aqueous methanolic 5 percent sodium hydroxide solution.

By treating the compounds of Formula D with an alkali metal hydride and then with an α-halocarboxylic acid ester, such as methyl α-bromopropionate and the like, the corresponding 2-alkoxycarbonyl-2-(1'-alkoxycarbonylalkyl)-1-tetralones are obtained. These compounds can be hydrolyzed, reduced, hydrogenolyzed, esterified, dehydrogenated and hydrolyzed by the means used to similarly treat compounds of Formula E, to obtain the corresponding 2-(2'-naphthyl)propionic acid derivatives.

The 1-tetralones of Formula C can be prepared directly from naphthalenes by conventional means known to the art. For example, the substituted 1-tetralones can be prepared from substituted naphthalenes. The substituted naphthalenes are reduced with 2 molar equivalents of hydrogen in the presence of a platinum, palladium, nickel catalyst, or the like, to afford the corresponding substituted tetralin. The substituted tetralin is then oxidized, such as with chromium trioxide in glacial acetic acid to obtain the substituted 1-tetralone.

The 1-tetralones substituted at position 6 of Formula C can also be prepared from the corresponding 7-substituted-1-tetralones (which are intermediates in the above-described preparation of naphthalenes substituted at position 6) by reducing and hydrogenolyzing the latter with sodium borohydride and hydrogen in the presence of palladium respectively to afford the corresponding tetralins. The tetralins are then oxidized with chromium trioxide in acetic acid to afford the corresponding 1-tetralones substituted at position 6. The tetralones are separated by conventional means, such as fractional crystallization or distillation.

Another method by which the present compounds can be prepared involves the reaction of 2-tetralones with one or more equivalents of a 1-alkoxycarbonylalkylidene triphenyl phosphorane, such as 1-methoxycarbonylethylidene triphenyl phosphorane, to furnish the corresponding 2,2-(1'-alkoxycarbonylalkylidene)tetralin. The latter upon heating with palladium-on-charcoal catalyst affords the corresponding 2-naphthylacetic acid ester derivative. The 1-alkoxycarbonylalkylidene triphenyl phosphorane reactant is obtained by reacting triphenylphosphine with a 2-halocarboxylic acid ester in an organic reaction medium followed by reaction with a base.

Thus, for example, by reacting 6-methoxy-2-tetralone with the triphenylphosphorane derived from ethyl 2-halopropionate, 2-(1'-carbethoxyeth-1'-ylidene)-6-methoxytetralin is prepared. Dehydrogenation of the latter compound provides ethyl 2-(6'-methoxy-2'-naphthyl)propionate which upon hydrolysis affords 2-(6'-methoxy-2'-naphthyl)propionic acid.

Substituted 2-tetralones of the following formula can be utilized in the above process:

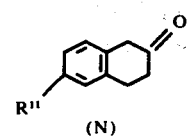

wherein $R^{11}$ is as defined above.

The substituted 2-tetralones of Formula N are prepared by treating the corresponding 1-tetralones with butylnitrite and hydrogen chloride gas in ether and then reacting the resulting 2-oximino-1-tetralones with an acid anhydride, such as acetic anhydride, in an organic acid, such as acetic acid in the presence of hydrogen and palladium-on-carbon catalyst to obtain the substituted 2-acetylamino-1-tetralone. The keto groups are then reduced to hydroxy groups with sodium borohydride or the like. The substituted 2-acetylamino-1-hydroxytetralines are then treated with glacial acetic acid in the presence of concentrated acid to obtain the corresponding substituted 2-tetralones of Formula N.

The addition of an alkyl substituent at the α-position of the acetic acid group to obtain the 2-(2'-naphthyl)propionic acid derivatives can be represented by the following:

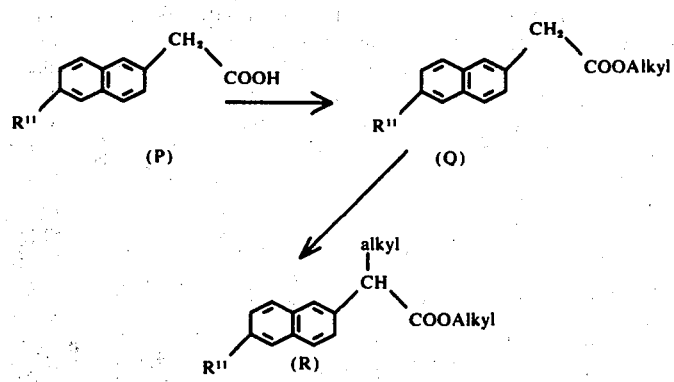

sponding 1-tetralones substituted at position 6. The wherein $R^{11}$ is as previously defined.

The 2-naphthylacetic acid derivatives of Formula P are esterified by conventional means, such as by reaction with an alkanol in the presence of boron trifluoride, to afford the corresponding esters of Formula Q. The compounds of Formula Q are treated with an akali metal hydride such as sodium hydride, potassium hydride, and the like, in an ether solvent, such as monoglyme, and then with an alkyl halide, such as methyl iodide, to afford the corresponding 2-(2'-naphthyl)propionic acid ester derivatives of Formula R. The latter are hydrolyzed by refluxing in a basic solution to obtain the corresponding 2-(2'-naphthyl)-propionic acid derivatives.

The 2-(6'-ethynyl-2'-naphthyl)priopionic acid derivatives can be prepared from 2-(6'-vinyl-2'-naphthyl)-propionic acid derivatives by brominating and dehydrobrominating the vinyl group as described above.

The α-difluoromethyl group can be introduced in the acetic acid moiety by treating the 2-naphthylacetic acid ester derivatives with an alkali metal or alkali metal hydride in a dialkyl carbonate, such as diethyl carbonate, to afford the corresponding 2-alkoxycarbonyl derivatives. The latter is treated with chlorodifluoromethane and an alkali metal alkoxide, such as potassium t-butoxide, in an ether solvent, preferably 1,2-dimethoxyethane to afford the corresponding 2-alkoxycarbonyl-2-difluoromethyl derivatives, which are hydrolyzed to furnish the corresponding 2-(2'-naphthyl)-2-carboxy-3,3-difluoropropionic acid derivatives. The deesterified product is decarboxylated by heating to between 30° C and 150° C, until the evolution of carbon dioxide ceases, to give the corresponding 2-(2'-naphthyl)-3,3-difluoropropionic acid derivatives.

By treating the above 2'-naphthyl-2-alkoxycarbonylacetic acid ester derivatives with an equivalent of an alkali metal hydride in a hydrocarbon solvent, then with an alkyl halide, the corresponding 2-(2'-naphthyl)-2-alkoxycarbonylpropionic acid ester derivatives are obtained. The latter are hydrolyzed and decarboxylated to furnish the corresponding 2-(2'-naphthyl)-propionic acid derivatives. This is an alternative method of introducing the α-alkyl substituent on the acetic acid moiety.

In the preferred embodiment of this invention the alkoxymethyloxy, alkylthiomethyloxy, alkoxymethylthio and alkylthiomethylthio are introduced after the introduction of substituents on the acetic acid moiety of the 2'-naphthylacetic acid derivatives.

Those compounds having a trifluoromethyl group can be prepared from the corresponding 6'-iodo compounds (Formula I, $R^1$ is iodo). The 2-(6'-iodo-2'-naphthyl)acetic acid derivatives by reaction with sulfonyl chloride are converted to the corresponding acid chloride, which is converted to the corresponding amide by reaction with an amine. Treatment of the amide with trifluoromethyl iodide in the presence of copper at elevated temperatures yields the corresponding 6'-trifluoromethyl compound which is then treated with acid to yield the corresponding 2-(6'-trifluoromethyl-2'-naphthyl)acetic acid derivative.

Those compounds contaning a trifluoromethyl group can also be prepared from the corresponding 6'-methylsubstituted 2'-naphthylacetic acid ester derivatives by treating the latter with chlorine and phosphorus trichloride in the presence of light to afford the corresponding trichloromethyl derivatives, which, when refluxed with antimony trifluoride in a hydrocarbon solvent, furnish the corresponding 6'-trifluoromethyl 2'-naphthylacetic acid ester derivatives.

Those compounds containing difluoromethoxy groups are preferably prepared from the corresponding 6'-alkoxy-2'-naphthylacetic acid ester derivatives by refluxing the latter with 48 percent hydrobromic acid in acetic acid to furnish the free hydroxy derivatives which, upon treatment with chlorodifluoromethane and an alkali metal hydroxide in aqueous dioxane or tetrahydrofuran, afford the corresponding 6'-difluoromethoxy2'-naphthylacetic acid derivatives.

By utilizing 6'-alkylthio-2'-naphthylacetic acid ester derivatives in the above process preferably replacing the hydrobromine acid and acetic acid with cyanogen bromide, the corresponding 6'-difluoromethylthio derivatives are obtained.

The hydroxy groups are etherified by conventional methods, for example, by treatment with an alkali metal hydride and then with an akylhalide, preferably an alkylbromide or iodide; or by treatment with a diazoalkane or an alkanol in the presence of boron trifluoride in an ether solvent, and the like.

The alkoxymethyloxy groups are introduced by treating the 6'-hydroxy-2'-naphthylacetic acid derivatives with an alkoxychloromethane in dimethylformamide to afford the corresponding 6'-alkoxymethyloxy-2'-naphthylacetic acid derivatives. The 6'-alkylthiomethyloxy-2'-naphthylacetic acid derivatives are prepared by utilizing an alkylthiochloromethane in the above process.

The 6'-alkoxymethylthio-2'-naphthylacetic acid derivatives are prepared by refluxing 6'-thio-2'-naphthylacetic acid derivatives with an alkoxychloromethane in dimethylformamide. The 6'-alkylthiomethylthio derivatives are prepared by using an alkylthiochloromethane in place of alkoxychloromethane in the above process.

The foregoing general procedures are useful for the preparation of the other naphthylacetic acid derivatives hereof.

Upon their preparation, the naphthylacetic acid derivatives can be converted to the corresponding esters and acid addition salts thereof.

The salt derivatives of the compounds of Formula I are prepared by treating the corresponding free acids of the compounds of Formula I (wherein $R^4$ is hydrogen) with at least one molar equivalent of a phramaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, manganous hydroxide, aluminum hydroxide, ferric hydroxide, manganic hydroxide, trimethylamine, triethylamine, tripropylamine, 2-dimethylaminoethanol, 2-diethylaminoethanol, arginine, lysine, histidine, caffeine, procaine, N-ethylpiperidine, hydrabamine, choline betaine, ethylenediamine, glucosamine, methylglucamine, theobromine, purines, piperazine, piperidine, polyamine resins and the like. The reaction is conducted in water, alone or in combination with an inert, water-miscible organic solvent, at a temperature of from about 0° C to about 100° C, preferably at room temperature. Typical inert, water-mixcible organic solvents include methanol, ethanol, isopropanol, butanol, acetone, dioxane or tetrahydrofuran. The molar ratio of compounds of Formula I to base used are chosen to provide the ratio desired for any particular salt. For preparing, for example, the calcium salts or magnesium salts of the compounds of Formula I, the free acid starting material can be treated with at least one molar equivalent of pharmaceutically acceptable base to yield a neutral salt. When the aluminum salts of the compounds of Formula I are prepared, at least one molar equivalent of the pharmaceutically acceptable base are employed if a neutral salt product is desired.

In the preferred procedure, the calcium salts and magnesium salts of the compounds of Formula I can be prepared by treating the corresponding sodium or potassium salts of the compound of Formula I with at least one molar equivalent of calcium chloride or magnesium chloride, respectively, in an aqueous solution, alone or in combination with an inert water-miscible organic solvent, at a temperature of from about 20° C to about 100° C. Preferably, the aluminum salts of the compounds of Formula I can be prepared by treating the corresponding free acids of the compounds of Formula I with at least one molar equivalent of an aluminum alkoxide, such as aluminum triethoxide, aluminum tripropoxide and the like, in a hydrocarbon solvent, such as benzene, xylene, cyclohexane, and the like at a temperature of from 20° C to about 115° C. Similar procedures can be used to prepare salts of inorganic bases which are not sufficiently soluble for easy reaction.

The salt products are isolated by conventional means. For example, the reaction mixtures are evaporated to dryness, and the salts can be further purified by conventional methods.

The esters of Formula I are prepared by esterifying the corresponding 2-(6'-substituted-2'-naphthyl)acetic acid derivatives (wherein $R^4$ is hydrogen) with an alcohol reagent corresponding to the desired ester, e.g. an alkanol having up to 22 carbon atoms, an alkenol having up to 22 carbon atoms, a cycloalkanol having from 3 to 7 carbon atoms, a cycloalkylmethanol having from 4 to 8 carbon atoms, a cycloalkylethanol having from 5 to 10 carbon atoms, phenol, an o-, m- and/or p-alkyl-substituted phenol having up to 8 carbon atoms, benzylalcohol, 2-phenylethanol, 3-phenylpropanol, etc. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in a non-aqueous liquid inert organic solvent in which the 2-(6'-substituted-2'-naphthyl)acetic acid derivative and the alochol reagent are soluble, such as a hydrocarbon solvent like hexane, iso-octane, decane, cyclohexane, benzene, toluene, xylene; a halogenated hydrocarbon solvent like methylene chloride, chloroform, dichloroethane; or an ether solvent like diethylether, dibutylether, dioxane, tetrahydrofuran. In the case where the alcohol reagent is a solid, the reaction preferably is conducted in a non-aqueous liquid inert organic solvent. The reaction is conducted at from about 0° C to the reflux temperature of the reaction mixture, preferably from 15° C to 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

The esters of Formula I can also be prepared by esterifying the corresponding 2-(6'-substituted-2'-naphthyl)acetyl halide derivatives with an alcohol reagent. This is the preferred method for preparing tertiary alcohol esters. The 2-(6'-substituted-2'-naphthyl)acetyl halide derivatives are prepared by treating the corresponding 2-(6'-substituted-2'-naphthyl)acetic acid derivatives with a thionyl halide, such as thionyl chloride; a phosphorous trihalide such as phosphorous tribromide; or a phosphorous pentahalide such as phosphorous pentachloride; preferably a thionyl halide is employed. The preparation of the 2-(6'-substituted-2'-naphthyl)acetyl halide derivatives is optionally carried out in an inert organic solvent such as a hydrocarbon solvent like benzene, toluene, hexane, cyclohexane, and the like; or a halogenated hydrocarbon like methylene chloride, chloroform, carbon tetrachloride, and the like. The reaction is normally preformed at temperatures between 0° C and 100° C, preferably between −15° C and 80° C. The acetyl halide products are isolated by conventional means. For example, when a thionyl halide is used to prepare the acetyl halide derivative, the reaction mixture is evaporated under reduced pressure to yield the product.

The 2-(6'-substituted-2'-naphthyl)acetyl halide derivatives are treated with alcohol reagents to prepare the esters of Formula I. The reaction is generally performed at temperatures between 0° C and the reflux temperature of the reaction mixture, preferably at room temperature. When the alcohol reagent employed is a liquid at the reaction temperature, the alcohol reagent can be the reaction solvent. Optionally, the reaction can be carried out in a non-aqueous inert organic solvent in which the 2-(6'-substituted-2'-naphthyl)acetyl halide derivatives and the alcohol reagents are soluble, such as hydrocarbons, halogenated hydrocarbons, pyridine or mixtures thereof. At least a molar equivalent of the alcohol reagent employed per molar equivalent of the 2-(6'-substituted-2'-naphthyl)acetyl halide derivative; and generally more than one molar equivalent of the alcohol reagent are employed. The ester products are isolated by conventional means. For example, the reaction mixture is diluted with water and extracted with diethyl ether. Ether extracts are combined, washed with water to neutrality, dried and evaporated to yield the compounds of Formulas I and II.

The preferred 2-(6'-substituted-2'-naphthyl)acetic acid ester derivatives are those ester derivatives prepared from methyl alcohol, ethyl alcohol, propyl alcohol, isopropyl alcohol, butyl alcohol, 2-butyl alcohol, pentyl alcohol, 2-pentyl alcohol, isopentyl alcohol, hexyl alcohol, 2-hexyl alcohol, isohexyl alcohol, heptyl alcohol, 2-heptyl alcohol, isoheptyl alcohol, octyl alcohol, 2-octyl alcohol, isooctyl alcohol, nonyl alcohol, 2-nonyl alcohol, isononyl alcohol, decyl alcohol 2-decyl alcohol, isodecyl alcohol, undecyl alcohol, dodecyl alcohol, tridecyl alcohol, tetradecyl alcohol, pentadecyl alcohol or hexadecyl alcohol.

This invention is further illustrated by the following specific but non-limiting examples.

PREPARATION 1

A mixture of 12.2 g. of methoxybenzene, 20 g. of succinic anhydride, 27 g. of aluminum chloride, and 250 ml. of carbon disulfide is stirred for four hours; the mixture is poured into 500 g. of ice, and the products are isolated by extraction with benzene. The product, 4-(4'-methoxyphenyl)-4-oxobutanoic acid is reduced with sodium borohydride, hydrogenolyzed with hydrogen in the presence of palladium charcoal catalyst, and cyclized by treatment with concentrated sulfuric acid to afford 7-methoxy-1-tetralone.

Ten grams of the above product is reduced by treatment with 6 g. of sodium borohydride in ethanol at 25° C for 6 hours. The mixture is acidified with aqueous 1 N hydrochloric acid and 6-methoxy-1-hydroxy-1,2,3,4-tetrahydro-2-naphthalene is isolated by benzene extraction. The product is hydrogenolyzed with hydrogen in the presence of palladium-on-carbon catalyst and dehydrogenated by heating with 10 percent palladium-on-charcoal catalyst to yield 2-methoxynaphthalene.

By the above procedure, but preferably dehydrogenating with 2 equivalents of sulfur at 200° C for one hour, 7-chloro-1-tetralone is prepared from chlorobenzene and is converted to 2-chloronaphthalene.

Likewise, by means of the above process, 7-fluoro-1-tetralone is prepared from fluorobenzene, and 2-fluoronaphthalene is prepared from 7-fluoro-1-tetralone.

Similarly, 7-isopropyl-1-tetralone, 7-methylthio-1-tetralone, 7-iodo-1-tetralone, and 7-methyl-1-tetralone are prepared from the corresponding substituted benzene derivatives by means of the above process.

PREPARATION 2

A mixture of 15.5 g. of 2-vinylnaphthalene, 23 g. of diiodomethane, 19.6 g. of zinc-copper couple (comprising 19.5 g. of zinc and 0.1 g. of copper) and 500 ml. of diethyl ether is refluxed for eight hours; the cooled mixture is then filtered, washed with dilute hydrochloric acid, washed with water to neutrality, dried and evaporated to yield 2-cyclopropylnaphthalene.

PREPARATION 3

To a mixture of 23.1 g. of naphthyl magnesium bromide and 250 ml. of diethyl ether, 7 g. of cyclobutanone are slowly added. After the addition, the mixture is refluxed for 1 hour, cooled, acidified with aqueous hydrochloric acid and filtered. The product is isolated by methylene chloride extraction to furnish 2-(1'-hydroxycyclobutyl)-naphthalene. The product is hydrogenated in 200 ml. of ethanol with a molar equivalent of hydrogen in the presence of 50 g. of Raney nickel; the reaction mixture is filtered after the hydrogenolysis and evaporated to furnish 2-cyclobutylnaphthalene.

PREPARATION 4

To a mixture of 15.5 g. of 2-vinylnaphthalene and 300 ml. of chloroform, a 5 percent bromine in chloroform solution is added at −10° C until the bromine color persists. The mixture is then added to 200 ml. of ammonia containing 15 g. of sodium amide. The mixture is allowed to evaporate, acidified with dilute hydrochloric acid, and the residue is extracted with diethyl ether. The extracts are combined, washed to neutrality with water, dried, and evaporated to yield 2-ethynylnaphthalene.

PREPARATION 5

A mixture of 14.6 g. of 2-tetralone, 20 g. of phenyl magnesium bromide, and 200 ml. of diethyl ether is stirred for 4 hours and then refluxed for one hour. The mixture is acidified with the addition of 200 ml. of 1 N hydrochloric acid, filtered, and extracted with diethyl ether. The extracts are combined, washed with water to neutrality, filtered, dried and evaporated; unchanged 2-tetralone is removed by distillation. The residue, containing 2-phenyl-3,4-dihydronaphthalene is mixed with 25 g. of 5 percent palladium-on-charcoal catalyst; the resulting mixture is heated to 200° C for 6 hours, cooled, diluted with 250 ml. of chloroform, filtered, and evaporated to give 2-phenylnaphthalene.

Similarly, 2-p-tolylnaphthalene is prepared by using p-tolyl magnesium bromide respectively in place of p-fluorophenyl magnesium bromide in the above process.

EXAMPLE 1

To a mixture of 1.6 g. of 2-methoxynaphthalene, 1.6 g. of acetyl chloride, and 20 ml. of nitrobenzene, 4.0 g. of aluminum chloride are slowly added. The resulting mixture is stirred for 48 hours at 25° C; then it is washed with water until free of chloride. The mixture is dried over sodium sulfate and evaporated under reduced pressure. The residue, 2-acetyl-6-methoxynaphthalene, is refluxed in 2 ml. of morpholine containing one-half gram of sulfur for 2 hours; the reaction mixture is then filtered and evaporated. The resulting thioamide derivative is extracted with diethyl ether; the extracts are combined and evaporated. The residue is refluxed in 10 ml. of concentrated hydrochloric acid for 2 hours, cooled to 25° C, and made alkaline with aqueous sodium hydroxide. The mixture is then extracted with ether and the extracts discarded. The aqueous layer is acidified and the precipitated 6-methoxy-2-naphthylacetic acid filtered.

Similarly, 2-naphthylacetic acid, 6-chloro-2-naphthylacetic acid, 6-fluoro-2-naphthylacetic acid, 6-ethoxy-2-naphthylacetic acid, 6-ethylthio-2-naphthylacetic acid, 6-methylthio-2-naphthylacetic acid, 6-methyl-2-naphthylacetic acid, 6-ethyl-2-naphthylacetic acid, 6-isopropyl-2-naphthylacetic acid, 6-cyclopropyl-2-naphthylacetic acid, 6-cyclohexyl-2-naphthylacetic acid, 6-hydroxy-2-naphthylacetic acid, 6-vinyl-2-naphthylacetic acid, 6-ethynyl-2-naphthylacetic acid and 6-phenyl-2-naphthylacetic acid are prepared from their respective corresponding naphthalene starting materials.

EXAMPLE 2

A mixture of 18 g. of 6-methoxy-1-tetralone, 60 g. of diethyl carbonate, 2.5 g. of sodium hydride, and 200 ml. of toluene is heated to 60° C for 5 hours. The mixture is cooled, acidified by the addition of 200 ml. of 1 N hydrochloric acid, and then extracted with three 75 ml. portions of benzene. The extracts are combined, washed with water to neutrality, and dried over sodium sulfate. The mixture, containing 6-methoxy-2-ethoxycarbonyl-1-tetralone, is treated with 2.5 g. of sodium hydride at room temperature with stirring. Twenty grams of ethyl α-bromoacetate are then added, and the mixture is allowed to stand for 12 hours at room temperature. The mixture is added to 500 ml. of water and extracted with methylene chloride. The extracts are combined, washed with water to neutrality, dried over sodium sulfate, and evaporated. The residue, containing 6-methoxy-2-ethoxycarbonyl-2-(ethoxycarbonylmethyl)-1-tetralone, is refluxed in 200 ml. of 6 N hydrochloric acid for 24 hours, and the refluxed mixture is evaporated. The residue, containing 6-methoxy-2-(carboxymethyl)-1-tetralone, is reduced by treating it with 200 ml. of ethanol containing 8 g. of sodium borohydride. After 1 hour, the mixture is acidified with the addition of 100 ml. of 3 N hydrochloric acid, and the resulting mixture is extracted with several portions of methylene chloride. The extracts are combined, washed with water to neutrality, dried over sodium sulfate, and evaporated. The residue, containing 6-methoxy-1-hydroxy-1,2,3,4-tetrahydro-2-naphthylacetic acid, is hydrogenolyzed by hydrogenating with one equivalent of hydrogen in acetic acid containing 300 mg. of 5 percent palladium-on-barium sulfate. The hydrogenation mixture is filtered and evaporated. The residue, containing 6-methoxy-1,2,3,4-tetrahydro-2-naphthylacetic acid, is dissolved in 200 ml. of diethyl ether, and the mixture is added to a 100 ml. solution of diethyl ether containing 4 g. of diazomethane. The mixture is then evaporated to dryness. The esterified residue is dehydrogenated by adding it to 1 g. of 10 percent palladium-on-charcoal and heating the resulting mixture for 6 hours at 200° C. The cooled mixture is diluted with 200 ml. of chloroform, filtered, and evaporated to afford methyl 6-methoxy-2-naphthylacetate.

Similarly, methyl 6-methyl-2-naphthylacetate, methyl 6-methylthio-2-naphthylacetate, and methyl 6-chloro-2-naphthylacetate are prepared from 6-methyl-1-tetralone, 6-methylthio-1-tetralone and 6-chloro-1-tetralone, respectively, by means of the above process.

A mixture of 25 g. of methyl 6-methoxy-2-naphthylacetate, 15 g. of sodium carbonate, 200 ml. of methanol, and 25 ml. of water are stirred for 24 hours. The reaction mixture is then acidified with 200 ml. of 2 N hydrochloric acid and extracted with methylene chloride. The extracts are combined, washed with water, dried over sodium sulfate, and evaporated to yield 6-methoxy-2-naphthylacetic acid.

Likewise, the methyl 6-substituted-2-naphthylacetates are hydrolyzed to the corresponding 2-naphthylacetic acids.

EXAMPLE 3

To a mixture of 22 g. of methyl 6-methyl-2-naphthylacetate, 2.5 g. of sodium hydride and 150 ml. of 1,2-dimethoxyethane, 25 g. of methyl iodide are added. The reaction mixture is allowed to stand for several hours and is then diluted with ethanol followed by water and extracted with methylene chloride. The extracts are combined, washed with water to neutrality, dried over sodium sulfate, filtered, and evaporated to yield methyl 6-methyl-2-naphthyl-α-methylacetate. This derivative is hydrolyzed by treatment with sodium carbonate in aqueous methanol, and the reaction mixture is acidified with hydrochloric acid, washed, dried and evaporated to dryness to yield 2-(6'-methyl-2'-naphthyl)-propionic acid.

2-(6'-methyl-2'-naphthyl)butyric acid is prepared by using ethyl iodide in place of methyl iodide in the above process. 2-(6'-ethoxy-2'-naphthyl)propionic acid, 2-(6'-ethyl-2'-naphthyl)propionic acid, 2-(6'-methoxymethyl-2'-naphthyl)propionic acid, 2-(6'-trifluoromethyl-2'-naphthyl)propionic acid, 2-(6'-isopropyl-2'-naphthyl)propionic acid, 2-(6'-vinyl-2'-naphthyl)propionic acid, 2-(6'-cyclopropyl-2'-naphthyl)-propionic acid, 2-(6'-fluoro-2'-naphthyl)propionic acid, 2-(6'-chloro-2'-naphthyl)propionic acid, 2-(6'-chloro-2'-naphthyl)butyric acid, 2-(6'-methoxy-2'-naphthyl)propionic acid, 2-(6'-methylthio-2'-naphthyl)propionic acid and 2-(6'-ethylthio-2'-naphthyl)- propionic acid are prepared from the corresponding methyl 2-naphthylacetate derivatives.

EXAMPLE 4

To a solution of 22.6 g. of 2-(6'-vinyl-2'-naphthyl)-propionic acid and 100 ml. of chloroform, there are added 320 g. of 5 percent solution of bromine and chloroform at −10° C. The resulting mixture is allowed to stand for 2 hours. The mixture is then evaporated to dryness. The residue is taken up in 250 ml. of diethyl ether and added to a mixture of liquid ammonia and 8 g. of sodium amide. The resulting ammonia mixture is allowed to stand for 10 hours; the mixture is then evaporated to dryness. The residue is acidified with dilute hydrochloric acid and extracted with diethyl ether, washed with water to neutrality, dried over sodium sulfate and evaporated to yield 2-(6'-ethynyl-2'-naphthyl)propionic acid.

In a similar manner, 2-(6'-ethynyl-2'-naphthyl)-2,2-difluoromethylene acetic acid is prepared from 2-(6'-vinyl-2'-naphthyl)-2,2-difluoromethylene acetic acid by means of the above process.

EXAMPLE 5

A mixture of 22 g. of methyl 6-fluoro-2-naphthylacetate, 10 g. of sodium methoxide, 6 g. of paraformaldehyde, and 200 ml. of dimethylsulfoxide is stirred for 18 hours at 25° C; the reaction mixture is acidified by the addition of 250 ml. of 1 N hydrochloric acid and extracted with methylene chloride. The extracts are combined, washed, dried, filtered, and evaporated to yield methyl 2-(6'-fluoro-2'-naphthyl)acrylate which is purified by chromatographing on alumina, eluting with methanol-diethyl ether. The product is hydrolyzed with sodium carbonate in aqueous methanol and the reaction mixture acidified with hydrochloric acid, filtered, washed with water, dried and evaporated to dryness to yield 2-(6'-fluoro-2'-naphthyl)acrylic acid.

Similarly, other 2-(2'-naphthyl)acrylic acids are prepared from the corresponding 2-naphthylacetic acid ester derivatives.

EXAMPLE 6

A mixture of 24.4 g. of ethyl 6-methoxy-2-naphthylacetate, 2.4 g. of sodium hydride, and 100 ml. of diethyl carbonate is stirred for 4 hours at 20° C. The product, diethyl 6-methoxy-2-naphthylmalonate (isolated by acidification with dilute hydrochloric acid followed by methylene chloride extraction), is added to 125 ml. of 1,2-dimethoxyethane containing 33 g. of potassium tert-butoxide; the mixture is allowed to stand for 4 hours at 60° C with chlorodifluoromethane being continually bubbled in after the mixture is initially saturated. The mixture is carefully neutralized by adding aqueous oxalic acid; the product, diethyl 2-(6'-methoxy-2'-naphthyl)-2-difluoromethylmalonate is isolated by methylene chloride extraction and hydrolyzed by refluxing in 250 ml. of methanol containing 5 g. of potassium hydroxide and 5 ml. of water. The cooled mixture is acidified with oxalic acid, and the product, 2-(6'-methoxy-2'-naphthyl)-2-difluoromethylmalonic acid, is extracted with methylene chloride. The dried product is decarboxylated by heating to 180° C for 6 hours to give 2-(6'-methoxy-2'-naphthyl)- 3,3-difluoropropionic acid.

Similarly, the 3,3-difluoropropionic acid derivatives of the following compounds are prepared from the corresponding acetic acid esters, e.g. 2-(6'-methyl-2'- naphthyl)-3,3-difluoropropionic acid, 2-(6'-isopropyl-2'-naphthyl)-3,3-difluoropropionic acid, 2-(6'-cyclopropyl-2'-naphthyl)-3,3-difluoropropionic acid, 2-(6'-trifluoromethyl-2'-naphthyl)-3,3-difluoropropionic acid, 2-(6'-methylthio-2'-naphthyl)-3,3-difluoropropionic acid, etc.

EXAMPLE 7

A mixture of 31.6 g. of diethyl 6-methoxy-2-naphthylmalonate, 2,4 g. of sodium hydride, and 350 ml. of methanol is stirred for one hour; then 24 1 g. of methyl iodide are added and the resulting mixture is refluxed for two hours. The cooled mixture is neutralized with aqueous oxalic acid. The product, diethyl 2-(6'-methoxy-2'-naphthyl)-2-methylmalonate, is isolated, hydrolyzed, and decarboxylated as described in Example 6 to give 2-(6'-methoxy-2'-naphthyl)propionic acid.

EXAMPLE 8

A mixture of 26 g. of methyl 2-(6'-methylthio-2'-naphthyl)propionate, 200 ml. of glacial acetic acid, and 2 ml. of a 48 percent hydrobromic acid are refluxed for two hours. The mixture is diluted with one liter of water and extracted with methyl chloride. The extracts are combined, washed with water, dried over sodium sulfate, filtered, and evaporated to yield 2-(6'-thio-2'-naphthyl)propionic acid. The latter compound is added to a mixture of 150 ml. of dioxane and 150 ml. of aqueous 20 percent sodium hydroxide. The resulting mixture is heated to 65° C and saturated with chlorodifluoromethane. The resulting mixture is allowed to stand for two hours while continuously bubbling in chlorodifluoromethane. The cooled reaction mixture is then acidified by the addition of aqueous 1 N hydrochloric acid and extracted with diethyl ether. The extracts are combined, washed with water to neutrality, dried over sodium sulfate, filtered, and evaporated to yield 2-(6'-difluoromethylthio-2'-naphthyl)propionic acid.

Repeating this procedure with methyl 2-(6'-methoxy-2'-naphthyl)propionate yields 2-(6'-difluoromethoxy-2'-naphthyl)propionic acid.

EXAMPLE 9

A mixture of 23 g. of methyl 2-(6'-hydroxy-2'-naphthyl)propionate, 25 g. of chlorodimethyl ether, and 500 ml. of dimethylformamide is allowed to stand at room temperature for 12 hours. The reaction mixture is evaporated under reduced pressure to give methyl 2-(6'-methoxymethyloxy-2'-naphthyl)propionate.

The methyl 2-(6'-hydroxy-2'-naphthyl)propionate is prepared by refluxing methyl 2-(6'-methoxy-2'-naphthyl)propionate with boron tribromide in methylene chloride and then hydrolyzing the resulting 6'-orthoboric ester with aqueous alkali.

Methyl 2-(6'-isopropoxymethyloxy-2'-naphthyl)propionate, methyl 2-(6'-ethoxymethyloxy-2'-naphthyl)propionate, and methyl 2-(6'-methylthiomethyloxy-2'-naphthyl)propionate are similarly prepared by utilizing chloromethyl isopropyl ether, chloromethyl ethyl ether, and methylthio chloromethane, respectively, in place of chlorodimethyl ether in the above process.

Methyl 2-(6'-methoxymethylthio-2'-naphthyl)propionate is prepared by utilizing methyl 2-(6'-thio-2'-naphthyl)propionate in the above process. Likewise, methyl 2-(6'-methylthio-2'-naphthyl)propionate is prepared by using methyl 2-(6'-thio-2'-naphthyl)propionate and methylthio chloromethane in the process described above.

EXAMPLE 10

Chlorine gas is bubbled through a mixture of 23 g of methyl 2-(6'-methyl-2'-naphthyl)propionate and 1 g. of phosphorus pentachloride in 200 ml. of carbon tetrachloride in the presence of light until 21.3 g. of chlorine have been taken up. The reaction mixture is diluted with 200 ml. of pyridine, filtered, further diluted with 500 ml. of ether, washed with water to neutrality, dried over sodium sulfate, and evaporated to yield methyl 2-(6'-trichloromethyl-2'-naphthyl)propionate. The above product is then refluxed in a mixture of 500 ml. of chlorobenzene and 17.9 g. of antimony trifluoride. The cooled reaction mixture is washed with water, dried over sodium sulfate, and evaporated to yield methyl 2-(6'-trifluoromethyl-2'-naphthyl)propionate.

EXAMPLE 11

A solution of 0.64 g. of 2-(6'-iodo-2'-naphthyl)propionic acid in 5 ml. of thionyl chloride and 10 ml. of benzene is refluxed for 1 hour and then evaporated to dryness under vacuum. The resulting acid chloride is then dissolved in 10 ml. of ether and added to a solution of 2 ml. of diethylamine in 20 ml. of ether. After washing with water, the ether solution is evaporated, and the residue crystallized from acetone giving N,N-diethyl-2-(6'-iodo-2'-naphthyl)propionamide.

100 Mg. of the amide, 200 mg. of copper powder, 1 ml. of dimethylformamide and 0.5 ml. of trifluoromethyl iodide in a sealed glass tube are heated to 135° C for 3 hours. The products are extracted into hexane which is washed with water. Evaporation of the solvent gives N,N-diethyl-2-(6'-trifluoromethyl-2'-naphthyl)-propionamide. The latter amide in 5 ml. of acetic acid and 5 ml. of concentrated hydrochloric acid is heated under reflux for 10 days. The mixture is then evaporated to dryness, and the residue distributed between sodium bicarbonate solution and ether. Acidification of the aqueous layer, and ether extraction gives 2-(6'-trifluoromethyl-2'-naphthyl)propionic acid which is recrystallized from acetone-hexane.

EXAMPLE 12

A mixture of 24.2 g of methyl 2-(6'-ethyl-2'-naphthyl)propionate 17.8 g. of N-bromosuccinimide, and 10 mg. of benzoyl peroxide, and 300 ml. of chloroform are refluxed for 2 hours in the presence of light. The mixture is filtered and evaporated. The residue is heated in 200 ml. of glacial acetic acid containing 16 g. of sodium acetate at 60° C for 24 hours. Five hundred milliliters of water are added to the resulting mixture and the product is extracted by diethyl ether extractions. The product, methyl 2-[6'-(1''-acetoxyethyl)-2'-naphthyl]propionate, is hydrolyzed by adding it to a 5 percent aqueous sodium carbonate solution. The product, 2-(6'-(1''-hydroxyethyl)-2'-naphthyl)propionic acid is isolated by acidification and diethyl ether extractions. The isolated product is oxidized by adding it to 200 ml. of glacial acetic acid containing 25 g. of chromium trioxide. The resulting mixture is allowed to stand at room temperature for 1 hour. Two hundred milliliters of a 10 percent sodium bisulfite solution are added and the mixture is extracted with diethyl ether. The extracts are combined, washed with water to neutrality, dried over sodium sulfate, filtered, and evaporated to give 2-(6'-acetyl-2'-naphthyl)propionic acid.

To a mixture of 24 g. of a 2-(6'-acetyl-2'-naphthyl)propionic acid and 200 ml. of diethyl ether are added 4.2 g. of diazomethane in 100 ml. of diethyl ether. The resulting mixture is evaporated to give methyl 2-(6'-acetyl-2'-naphthyl)propionate. The product is added to 200 ml. of aqueous 20 percent sodium hypochlorite. The resulting mixture is allowed to stand for 4 hours at room temperature. The mixture is acidified by the addition of aqueous 1 N hydrochloric acid and extracted with diethyl ether. The extracts are combined, washed with water to neutrality, dried over sodium sulfate, filtered, and evaporated to give 2-(6'-carboxy-2'-naphthyl)propionic acid.

The latter compound is etherified with 8.4 g. of diazomethane in diethylether, as described above to give methyl 2-(6'-methoxycarbonyl-2'-naphthyl)propionate. The diester is hydrolyzed by refluxing in 200 ml. of ethyl alcohol containing 4 g. (one molar equivalent) of sodium hydroxide for 5 hours. The cooled mixture is acidified by the addition of aqueous 1 N hydrochloric acid and the product is isolated by methylene chloride extraction to give 2-(6'-methoxycarbonyl-2'-naphthyl)propionic acid.

A mixture of 25.8 g. of 2-(6'-methoxycarbonyl-2'-naphthyl)propionic acid, 4 g. of sodium hydroxide, 10 ml. of water, and 500 ml. of methanol are heated to 50° C, cooled, and evaporated. The residue is taken up in 500 ml. of diethylene glycol dimethyl ether and diborane is bubbled through. The resulting mixture is treated with diborane and is allowed to stand for 18 hours. The reaction mixture is acidified by the addition of aqueous 1 N hydrochloride acid. The mixture is extracted with methylene chloride. The extracts are combined, washed with water to neutrality, dried over sodium sulfate, filtered, and evaporated to give 2-(6'-hydroxymethyl-2'-naphthyl)propionic acid.

To a mixture of 24.4 g. of methyl 2-(6'-hydroxymethyl-2'-naphthyl)propionate [prepared from 2-(6'-hydroxymethyl-2'-naphthyl)propionic acid by esterifying the latter with diazomethane in ethanol as described above] and 500 ml. of benzene are added 2.4 g. of sodium hydride. The resulting mixture is stirred for two hours; then 12.2 g. of methyl iodide are added. The resulting mixture is neutralized by the addition of aqueous 1 N hydrochloric acid after it has been allowed to stand for one hour; the mixture is then washed with water, dried over sodium sulfate, and evaporated to give methyl 2-(6'-methoxymethyl)-2'-naphthyl)propionate.

Methyl 2-(6'-ethoxymethyl-2'-naphthyl)propionate is prepared by using 13.7 g. of ethyl iodide in place of methyl iodide in the above process.

EXAMPLE 13

A mixture of 23 g. of 2-(6'-hydroxymethyl-2'-naphthyl)propionic acid, 230 g. of manganese dioxide, and 2 l. of chloroform are stirred for 12 hours; the mixture is filtered and evaporated to give 2-(6'-formyl-2'-naphthyl)propionic acid.

A mixture of 22.8 g. of 2-(6'-formyl-2'-naphthyl)propionic acid, 14 g. of hydroxylamine hydrochloride, 25 g. of sodium acetate, and 1 l. of ethyl alcohol are refluxed for one hour; the cooled reaction mixture is diluted with 1 l. of water and extracted with methylene chloride. The extracts are combined, washed with water to neutrality, dried over sodium sulfate, filtered, and evaporated to give the oxime of 2-(6'-formyl-2'-naphthyl)propionic acid. The above oxime is refluxed in 1 l. of acetic anhydride containing 20 g. of p-toluenesulfonic acid for 1 hour; the reaction mixture is then evaporated to dryness. The residue is taken up in methylene chloride, washed with water, dried over sodium sulfate, filtered, and evaporated to yield 2-(6'-cyano-2'-naphthyl)propionic acid.

Similarly, by means of the above processes, 2-(6'-acetyl-2'-naphthyl)-3,3-difluoropropionic acid, 2-(6'-carboxy-2'-naphthyl)3,3-difluoropropionic acid, 2-(6'-methoxycarbonyl-2'-naphthyl)3,3-difluoropropionic acid, 2-(6'-hydroxymethyl-2'-naphthyl)3,3-difluoropropionic acid, 2-(6'-formyl-2'-naphthyl)-3,3-difluoropropionic acid, and the oxime thereof, and 2-(6'-cyano-2'-naphthyl)-3,3-difluoropropionic acid are prepared from methyl 2-(6'-ethyl-2'-naphthyl)-3,3-difluoropropionate.

EXAMPLE 14

To a mixture of 20 g. of sodium hydroxide and 400 ml. of methanol are added 24.5 g. of methyl 2-(6'-methoxy-2'-naphthyl)propionate. The resulting reaction mixture is heated to 60° C for 5 hours. The cooled mixture is acidified with aqueous 1 N hydrochloric acid and extracted with methylene chloride. The extracts are combined, washed with water to neutrality, dried over sodium sulfate, filtered, and evaporated to give 2-(6'-methoxy-2'-naphthyl)propionic acid.

Similarly, the other ester derivatives prepared by means of the procedures described in the other examples herein are hydrolyzed to the corresponding carboxylic acids.

EXAMPLE 15

A mixture of 2.3 g. of 2-(6'-methoxy-2'-naphthyl)propionic acid, 2.9 g. of cinchonidine, and 50 ml. of methanol is stirred for two hours; the mixture is then allowed to stand until crystallization is complete. The crystals are filtered off and washed with methanol. The crystals are recrystallized from methanol, filtered, washed, and dried. The pure crystals are added to 60 ml. of 0.2 N hydrochloric acid. The resulting mixture is stirred for 2 hours and then extracted with diethyl ether. The extracts are combined, washed with water to neutrality, dried over sodium sulfate, and evaporated to yield d 2-(6'-methoxy-2'-naphthyl)propionic acid. The filtrates from the above are acidified with aqueous dilute hydrochloric acid and the product is isolated by diethyl ether extractions to give l 2-(6'-methoxy-2'-naphthyl)propionic acid.

Similarly, the optical isomers of the other α-monosubstituted 2-naphthylacetic acid derivatives made by the procedures described herein are separated.

EXAMPLE 16

A solution of 50:50 d and l 2-(6'-methoxy-2'-naphthyl)propionic acid in methanol is prepared by dissolving 230 g. of the racemic mixture in 4.6 l. of warm methanol. The resulting solution is boiled until it becomes turbid; then sufficient methanol is added to make the solution clear again. This hot solution is added to a solution of 296 g. of cinchonidine in 7.4 l. of methanol heated to about 60° C. The solutions are combined while stirring, and the combined mixture is then allowed to obtain room temperature over a 2 hour period. After the reaction mixture has obtained room temperature, it is stirred for an additional two hours and then filtered. The filtered salt is washed with several portions of ice cold methanol. The resulting washed salt is then dried under vacuum.

A saturated solution of the above salt in methanol is prepared by initially dissolving 100 g. of the above salt in 4 l. of methanol heated to about 60° C. The mixture is then refluxed, and additional salt is added until the solution becomes turbid; at this point, methanol is added to make the solution clear again. The resulting mixture is allowed to cool to room temperature. After the cooled mixture is allowed to stand for two hours, it is filtered. The filtered salt is washed to yield the cinchonidine salt of d 2-(6'-methoxy-2'-naphthyl)propionic acid.

The above recrystallization is repeated 9 times using 2.5 l. of methanol in place of 4 l. to yield the cinchonidine salt of d 2-(6'-methoxy-2'-naphthyl)propionic acid.

The filtrates from the above procedures are combined and evaporated. The resulting salt is added to 1500 ml. of hot ethanol; the hot mixture is slowly allowed to cool to 0° C over 12 hours, then the cooled mixture is filtered. The filtered salt crystals are washed 5 times with ice cold ethanol. The salt is then recrystallized an additional 4 times, first from 1350 ml. of ethanol:water (26:1), secondly from 1150 ml. of ethanol:water (55:2), thirdly from 900 ml. of ethanol:water (27:1) and lastly from 675 ml. of ethanol:water (26:1) to yield the salt of cinchonidine and l 2-(6'-methoxy-2'-naphthyl)propionic acid.

One hundred grams of the cinchonidine salt of l 2-(6'-methoxy-2'-naphthyl)propionic acid is added to a stirred mixture of 600 ml. of ethyl acetate and 450 ml. of 2 N aqueous hydrochloric acid. After the mixture has been stirred for 2 hours, the ethyl acetate layer is removed and washed with water to neutrali dried over sodium sulfate, and evaporated to yield l 2-(6'-methoxy-2'-naphthyl)propionic acid.

Similarly, d 2-(6'-methoxy-2'-naphthyl)propionic acid is prepared from the cinchonidine salt of d 2-(6'-methoxy-2'-naphthyl)propionic acid.

The racemate of other 2-(6'-substituted-2'-naphthyl)propionic acid derivatives made by the procedures described herein are resolved by means of the above procedure. For example, d 2-(6'-methyl-2'-naphthyl)propionic acid and l 2-(6'-methyl-2'-naphthyl)propionic acid, d 2-(6'-methylthio-2'-naphthyl)propionic acid and l 2-(6'-methyl-2'-naphthyl)propionic acid, d 2-(6'-difluoromethoxy-2'-naphthyl)propionic acid and l 2-(6'-difluoromethoxy-2'-naphthyl)propionic acid, and d 2-(6'-methylthio-2'-naphthyl)-3,3-difluoropropionic acid and l 2-(6'-methylthio-2'-naphthyl)-3,3-difluoropropionic acid can be resolved from racemic mixtures of the corresponding 2-(6'-methyl-2'-naphthyl)propionic acid, 2-(6'-methylthio-2'-naphthyl)propionic acid, 2-(6'-difluoromethoxy-2'-naphthyl)propionic acid and 2-(6'-methylthio-2'-naphthyl)-3,3-difluoropropionic acid by means of the above described process.

EXAMPLE 17

To a mixture of 4 g. of sodium hydroxide and 500 ml. of methanol are added 24.6 g. of 2-(6'-methylthio-2'-naphthyl)propionic acid. The mixture is stirred for 1 hour at 50° C. The cooled mixture is then evaporated to give the sodium salt of 2-(6'-methylthio-2'-naphthyl)propionic acid.

By employing potassium hydroxide, diethylamine, lysine, caffeine, or procaine in place of sodium hydroxide in the above process, the potassium, triethylamine, lysine, caffeine, or procaine salt of 2-(6'-methylthio-2'-naphthyl)propionic acid is obtained.

By means of the above procedure, the addition salts of 2-(6'-substituted-2'-naphthyl)acetic acid derivatives prepared in Examples 1-16 can be prepared.

EXAMPLE 18

To a mixture of 4 g. of sodium hydroxide and 500 ml. of aqueous methanol, there is added 23 g. of d 2-(6'-methoxy-2'-naphthyl)propionic acid. The mixture is stirred for three hours at room temperature; the mixture is then evaporated to give sodium d 2-(6'-methoxy-2'-naphthyl)propionate.

By employing 5.6 g. of potassium hydroxide in place of sodium hydroxide in the above procedure, potassium d 2-(6'-methoxy-2'-naphthyl)propionate is obtained. By employing 3.71 g. of calcium hydroxide in place of sodium hydroxide in the above process, calcium di[d 2-(6'-methoxy-2'-naphthyl)-propionate] is obtained.

Similarly, the sodium, potassium and calcium salts of the 2-(6'-substituted-2'-naphthyl)acetic acid derivatives of Examples 1-16 are prepared by means of the above process. For example sodium l 2-(6'-methoxy-2'-naphthyl)propionate,
sodium d and l 2-(6'-methyl-2'-naphthyl)propionate,
sodium d and l 2-(6'-trifluoromethyl-2'-naphthyl)propionate,
sodium d and l 2-(6'-methoxy-2'-naphthyl)propionate,
sodium d and l 2-(6'-difluoromethoxy-2'-naphthyl)propionate,
sodium d and l 2-(6'-chloro-2'-naphthyl)propionate,
sodium d and l 2-(6'-methylthio-2'-naphthyl)propionate,
sodium d and l 2-(6'-difluoromethylthio-2'-naphthyl)propionate,
sodium d and l 2-(6'-vinyl-2'-naphthyl)propionate,
sodium d and l 2-(6'-ethyl-2'-naphthyl)-3,3-difluoropropionate,
sodium d and l 2-(6'-cyclopropyl-2'-naphthyl)-3,3-difluoropropionate,
sodium d and l 2-(6'-fluoro-2'-naphthyl)-3,3-difluoropropionate,
sodium d and l 2-(6'-methoxy-2'-naphthyl)-3,3-difluoropropionate,
sodium d and l 2-(6'-difluoromethoxy-2'-naphthyl)-3,3-difluoropropionate,
sodium d and l 2-(6'-methylthio-2'-naphthyl)-3,3-difluoropropionate,
sodium d and l 2-(6'-methyl-2'-naphthyl)-3,3-difluoropropionate,
sodium d and l 2-(6'-isopropyl-2'-naphthyl)-3,3-difluoropropionate,
sodium d and l 2-(6'-chloro-2'-naphthyl)-3,3-difluoropropionate,
sodium d and l 2-(6'-vinyl-2'-naphthyl)-3,3-difluoropropionate,
sodium d and l 2-(6'-trifluoromethyl-2'-naphthyl)-3,3-difluoropropionate,
sodium d and l 2-(6'-acetyl-2'-naphthyl)-3,3-difluoropropionate, and
sodium d and l 2-(6'-ethynyl-2'-naphthyl)-3,3-difluoropropionate, are prepared from the corresponding 2-(6'-substituted-2'-naphthyl)propionic acid derivatives by means of the above process.

EXAMPLE 19

To a mixture of 5.55 g. of calcium chloride and 300 ml. of water, there is added a solution of 25.2 g. of sodium d 2-(6'-methoxy-2'-naphthyl)propionate and 300 ml. of water; the resulting mixture is allowed to stand for 12 hours at room temperature. The mixture is then filtered, and the filtered salt is washed with several portions of ice cold water. The washed salt is dried under vacuum to yield the calcium d 2-(6'-methoxy-2'-naphthyl)propionate.

By employing 4.77 g. of magnesium chloride in the above process, the magnesium d 2-(6'-methoxy-2'-naphthyl)propionate is obtained.

By means of the above process, the calcium and magnesium salts of the 2-(6'-substituted-2'-naphthyl)acetic acid derivatives of Examples 1–16 are prepared after initially preparing the sodium or potassium salts by means of the process described in Example 18. For example, the calcium salt of 2-(6'-methyl-2'-naphthyl)propionic acid,
the calcium salt of 2-(6'-ethyl-2'-naphthyl)propionic acid,
the calcium salt of 2-(6'-trifluoromethyl-2'-naphthyl)propionic acid,
the calcium salt of 2-(6'-methoxy-2'-naphthyl)propionic acid,
the calcium salt of 2-(6'-difluoromethoxy-2'-naphthyl)propionic acid,
the calcium salt of 2-(6'-chloro-2'-naphthyl)propionic acid,
the calcium salt of 2-(6'-fluoro-2'-naphthyl)propionic acid,
the calcium salt of 2-(6'-methylthio-2'-naphthyl)propionic acid,
the calcium salt of 2-(6'-difluoromethylthio-2'-naphthyl)propionic acid,
the calcium salt of 2-(6'-methyl-2'-naphthyl)-3,3-difluoropropionic acid,
the calcium salt of 2-(6'-trifluoromethyl-2'-naphthyl)-3,3-difluoropropionic acid,
the calcium salt of 2-(6'-chloro-2'-naphthyl)-3,3-difluoropropionic acid,
the calcium salt of 1 2-(6'-methoxy-2'-naphthyl)-3,3-difluoropropionic acid,
the calcium salt of 2-(6'-methoxy-2'-naphthyl)-3,3-difluoropropionic acid,
the calcium salt of 2-(6'-difluoromethylthio-2'-naphthyl)-3,3-difluoropropionic acid,
the calcium salt of 2-(6'-ethynyl-2'-naphthyl)-3,3-difluoropropionic acid,
the calcium salt of 2-(6'-methyl-2'-naphthyl)-3,3-difluoropropionic acid, and
the calcium salt of 2-(6'-methylthio-2'-naphthyl)-3,3-difluoropropionic acid are prepared from the corresponding sodium or potassium 2-(6'-substituted-2'-naphthyl)propionate derivatives (prepared by the process described in Example 18) by means of the above process.

EXAMPLE 20

Repeating the procedure of Example 19 but replacing calcium chloride with ferrous chloride, zinc chloride, manganous chloride, ferric chloride or manganic chloride yields the respective ferrous, zinc, manganous, ferric, manganic 2-(6'-substituted-2'-naphthyl)propionates, i.e.

ferrous d 2-(6'-methoxy-2'-naphthyl)propionate,
zinc d 2-(6'-methoxy-2'-naphthyl)propionate,
manganous d 2-(6'-methoxy-2'-naphthyl)propionate,
ferric d 2-(6'-methoxy-2'-naphthyl)propionate, and
manganic d 2-(6'-methoxy-2'-naphthyl)propionate.

EXAMPLE 21

To a mixture of 16.2 g. of aluminum triethoxide and 1 l. of benzene, there are added 69 g. of d 2-(6'-methoxy-2'-naphthyl)propionic acid. The resulting mixture is refluxed for 24 hours; the mixture is then cooled and evaporated under reduced pressure to give the aluminum salt of d 2-(6'-methoxy-2'-naphthyl)propionic acid.

By means of the above procedure, the aluminum salts of the 2-(6'-substituted-2'-naphthyl)acetic acid derivatives of Examples 1–16 can be prepared. For example, the aluminum salt of 2-(6'-methyl-2'-naphthyl)propionic acid,
the aluminum salt of 2-(6'-difluoromethoxy-2'-naphthyl)propionic acid,
the aluminum salt of 2-(6'-fluoro-2'-naphthyl)propionic acid,
the aluminum salt of 2-(6'-ethynyl-2'-naphthyl)propionic acid,
the aluminum salt of 2-(6'-isopropyl-2'-naphthyl)-3,3-difluoropropionic acid,
the aluminum salt of 1 2-(6'-methoxy-2'-naphthyl)propionic acid,
the aluminum salt of 2-(6'-methoxy-2'-naphthyl)-3,3-difluoropropionic acid,
the aluminum salt of 2-(6'-chloro-2'-naphthyl)-3,3-difluoropropionic acid,
the aluminum salt of 2-(6'-methylthio-2'-naphthyl)-3,3-difluoropropionic acid, and
the aluminum salt of 2-(6'-acetyl-2'-naphthyl)-3,3-difluoropropionic acid are prepared from the corresponding 2-(6'-substituted-2'-naphthyl)propionic acid derivatives by means of the above described process.

EXAMPLE 22

To a mixture of 50 ml. of concentrated aqueous ammonia in 500 ml. of methanol, there are added 23 g. of d 2-(6'-methoxy-2'-naphthyl)propionic acid. The resulting mixture is stirred for two hours and is then evaporated to dryness to yield the ammonium salt of d 2-(6'-methoxy-2'-naphthyl)propionate.

By employing trimethylamine, triethylamine or tripropylamine in place of ammonia in the above process, trimethylammonium d 2-(6'-methoxy-2'-naphthyl)propionate, triethylammonium d 2-(6'-methoxy-2'-naphthyl)propionate, and tripropylammonium d 2-(6'-methoxy-2'-naphthyl)propionate, respectively, are obtained. By means of the above process the ammonia, trimethylamine, triethylamine and tripropylamine salts of the 2-(6'-substituted-2'-naphthyl)acetic acid derivatives of Examples 1–16 can be prepared. For example ammonium 1 2-(6'-methoxy-2'-naphthyl)propionate,
ammonium 2-(6'-methyl-2'-naphthyl)propionate,
ammonium 2-(6'-acetyl-2'-naphthyl)propionate,
ammonium 2-(6'-isopropyl-2'-naphthyl)propionate, ammonium 2-(6'-trifluoromethyl-2'-naphthyl)propionate,
ammonium 2-(6'-chloro-2'-naphthyl)propionate,
ammonium 2-(6'-methylthio-2'-naphthyl)propionate,
ammonium 2-(6'-methyl-2'-naphthyl)-3,3-difluoropropionate,
ammonium 2-(6'-fluoro-2'-naphthyl)-3,3-difluoropropionate,
ammonium 2-(6'-difluoromethoxy-2'-naphthyl)-3,3-difluoropropionate,
ammonium 2-(6'-methoxy-2'-naphthyl)-3,3-difluoropropionate, and
ammonium 2-(6'-vinyl-2'-naphthyl)-3,3-difluoropropionate are prepared from the corresponding 2-(6'-substituted-2'-naphthyl)propionic acid derivatives.

EXAMPLE 23

To a mixture of 27.3 g. of procaine and 500 ml. of aqueous methanol, there are added 23 g. of d 2-(6'-methoxy-2'-naphthyl)propionic acid; the resulting mixture is stirred for 16 hours at room temperature. The mixture is then evaporated under reduced pressure to give the procaine salt of 2-(6'-methoxy-2'-naphthyl)propionic acid.

In a similar manner, by employing 14.6 g. of lysine, 17.4 g. of arginine or 19.4 g. of caffeine in place of procaine in the above process, the lysine, arginine or caffeine salt of d 2-(6'-methoxy-2'-naphthyl)propionic acid is respectively, obtained.

Similarly, the lysine, caffeine, arginine and procaine salts of the 2-(6'-substituted-2'-naphthyl)acetic acid derivatives of Examples 1–16 can be prepared. For example, the procaine salt of 2-(6'-cyclopropyl-2'-naphthyl)propionic acid,
the procaine salt of 2-(6'-fluoro-2'-naphthyl)propionic acid,
the procaine salt of 2-(6'-difluoromethylthio-2'-naphthyl)propionic acid,
the procaine salt of 2-(6'-isopropyl-2'-naphthyl)-3,3-difluoropropionic acid,
the procaine salt of 1 2-(6'-methoxy-2'-naphthyl)propionic acid,
the procaine salt of 2-(6'-trifluoromethyl-2'-naphthyl)-3,3-difluoropropionic acid,
the procaine salt of 2-(6'-methyl-2'-naphthyl)propionic acid,
the procaine salt of 2-(6'-chloro-2'-naphthyl)-3,3-difluoropropionic acid,
the procaine salt of 2-(6'-methoxy-2'-naphthyl)-3,3-difluoropropionic acid,
the procaine salt of 2-(6'-difluoromethoxy-2'-naphthyl)-3,3-difluoropropionic acid,
the procaine salt of 2-(6'-methyl-2'-naphthyl)-3,3-difluoropropionic acid, and
the procaine salt of 2-(6'-difluoromethylthio-2'-naphthyl)-3,3-difluoropropionic acid are prepared from the corresponding 2-(6'-substituted-2'-naphthyl)propionic acid derivatives.

EXAMPLE 24

The ethanolamine salt of d 2-(6'-methoxy-2'-naphthyl)propionic acid is prepared from d 2-(6'-methoxy-2'-naphthyl)propionic acid by means of the process described in Example 23, except 6.1 g. of ethanolamine is used in place of procaine.

In a similar manner, the ethanolamine salts of the 2-(6'-substituted-2'-naphthyl)acetic acid derivatives of Examples 1–16 are prepared.

EXAMPLE 25

The 2-(diethylamino)ethanol salt of d 2-(6'-methoxy-2'-naphthyl)propionic acid is prepared from d 2-(6'-methoxy-2'-naphthyl)propionic acid by means of the process described in Examples 23, except 11.8 g. of 2-(diethylamino)ethanol is used in place of procaine.

In a similar manner, the 2-(diethylamino)ethanol salts of the 2-(6'-substituted-2'-naphthyl)acetic acid derivatives of Examples 1–16 are prepared.

EXAMPLE 26

The 2-(dimethylamino)ethanol salt of d 2-(6'-methoxy-2'-naphthyl)propionic acid is prepared from d 2-(6'-methoxy-2'-naphthyl)propionic acid by means of the process described in Examples 23 except 9.0 g. of 2-(dimethylamino)ethanol is used in place of procaine.

In a similar manner, the 2-(dimethylamino)ethanol salts of the 2-(6'-substituted-2'-naphthyl)acetic acid derivatives of Examples 1–16 are prepared.

EXAMPLE 27

The methyl glucamine salt of d 2-(6'-methoxy-2'-naphthyl)propionic acid is prepared from d 2-(6'-methoxy-2'-naphthyl)propionic acid by means of the process described in Example 23 except 19.5 g. of methyl glucamine is used in place of procaine.

In a similar manner, the methyl glucamine salts of the 2-(6'-substituted-2'-naphthyl)acetic acid derivatives of Examples 1–16 are prepared.

EXAMPLE 28

The ethylenediamine salt of d 2-(6'-methoxy-2'-naphthyl)propionic acid is prepared from d 2-(6'-methoxy-2'-naphthyl)propionic acid by means of the process described in Example 23, except, 6.0 g. of ethylenediamine is used in place of procaine.

In a similar manner, the ethylenediamine salts of the 2-(6'-substituted-2'-naphthyl)acetic acid derivatives of Examples 1–16 are prepared.

EXAMPLE 29

At room temperature, boron trifluoride etherate is added to a mixture of 23 g. of d 2-(6'-methoxy-2'-naphthyl)propionic acid in 100 ml. of isoamyl alcohol for a period of 24 hours. The mixture is then diluted with 250 ml. of water and extracted with several portions of methylene chloride. The extracts are combined, washed with water to neutrality, dried over sodium sulfate and evaporated under reduced pressure to yield d isoamyl 2-(6'-methoxy-2'-naphthyl)propionate.

Similarly, by means of the above described process, 1 isoamyl 2-(6'-methoxy-2'-naphthyl)propionate is prepared from 1 2-(6'-methoxy-2'-naphthyl)propionic acid.

In a similar manner, the 2-(6'-substituted-2'-naphthyl)acetic acid derivatives prepared in Examples 1–16 are etherified by means of the above process to prepare the corresponding isoamyl 2-(6'-substituted-2'-napthyl)acetate derivatives. For example, isoamyl 2-(6'-methoxy-2'-naphthyl)acetate,
d and l isoamyl 2-(6'-methoxy-2'-naphthyl)propionate, d and l isoamyl 2-(6'-methoxy-2'-naphthyl)-3,3-difluoropropionate,
d and l isoamyl 2-(6'-methoxy-2'-naphthyl)acrylate,
isoamyl 2-(6'-isopropyl-2'-naphthyl)acetate.
d and l isoamyl 2-(6'-isopropyl-2'-naphthyl)propionate,
d and l isoamyl 2-(6'-isopropyl-2'-naphthyl)-3,3-difluoropropionate,
d and l isoamyl 2-(6'-isopropyl-2'-naphthyl)acrylate,
isoamyl 2-(6'-ethynyl-2'-naphthyl)acetate,
d and l isoamyl 2-(6'-ethynyl-2'-naphthyl)propionate,
d and l isoamyl 2-(6'-ethynyl-2'-naphthyl)-3,3-difluoropropionate,
d and l isoamyl 2-(6'-ethynyl-2'-naphthyl)acrylate,
isoamyl 2-(6'-difluoromethylthio-2'-naphthyl)acetate,
d and l isoamyl 2-(6'-difluoromethylthio-2'-naphthyl)propionate,
d and l isoamyl 2-(6'-difluoromethylthio-2'-naphthyl)-3,3-difluoropropionate, and
d and l isoamyl 2-(6'-difluoromethylthio-2'-naphthyl)acrylate are prepared from the corresponding 2-(6'-substituted-2'-naphthyl)acetic acid derivatives.

EXAMPLE 30

A mixture of 246 g. of d 2-(6'-methoxy-2'-naphthyl)-propionic acid and 1.5 l. of benzene is treated with 144 g. of thionyl chloride at room temperature until the evolution of gas ceases. The mixture is cooled and evaporated to dryness under high vacuum to yield the acid chloride of 2-(6'-methoxy-2'-naphthyl)propionic acid.

The above acid chloride in 500 ml. of benzene is added dropwise to a mixture of one liter of pyridine and 500 ml. of palmityl alcohol while stirring and maintaining the reaction mixture at about room temperature. After the addition of the acid chloride product, the reaction mixture is heated to 90° for 5 hours and then cooled to room temperature. The reaction mixture is then diluted with one liter of water; then the organic layer is drawn off. The organic extract is washed with water to neutrality, dried over sodium sulfate and evaporated to dryness under reduced pressure to yield d palmityl 2-(6'-methoxy-2'-naphthyl)propionate. The ester is further purified by chromatographing on acid grade alumina eluting with hexane:diethyl ether (6:1).

Similarly, l palmityl 2-(6'-methoxy-2'-naphthyl)propionate is prepared from l 2-(6'-methoxy-2'-naphthyl)propionic acid by means of the above described process.

In a similar manner the 2-(6'-substituted-2'-naphthyl)acetic acid derivatives of Examples 1–16 are esterified by means of the above process to yield the corresponding palmityl 2-(6'-substituted-2'-naphthyl)acetate derivatives. For example, palmityl 2-(6'-methylthio-2'-naphthyl)acetate,
palmityl 2-(6'-methylthio-2'-naphthyl)propionate,
palmityl 2-(6'-methylthio-2'-naphthyl)-3,3-difluoropropionate,
palmityl 2-(6'-methylthio-2'-naphthyl)acrylate,
palmityl 2-(6'-vinyl-2'-naphthyl)acetate,
palmityl 2-(6'-vinyl-2'-naphthyl)propionate,
palmityl 2-(6'-vinyl-2'-naphthyl)-3,3-difluoropropionate, and
palmityl 2-(6'-vinyl-2'-naphthyl)acrylate are prepared from the corresponding 2-(6'-substituted-2'-naphthyl)acetic acid derivatives by means of the above process.

EXAMPLE 31

At room temperature, anhydrous hydrogen chloride is bubbled through a mixture of 520 g. of 2-(6'-trifluoromethyl-2'-naphthyl)propionic acid, 2.5 liters of carbon tetrachloride and 2.5 liters of hexanol until the mixture is saturated with hydrogen chloride. The resulting mixture is allowed to stand for 24 hours under anhydrous conditions, then the mixture is diluted with 15 l. of water and extracted with chloroform. The extracts are combined, washed with water and aqueous sodium bicarbonate, washed with water to neutrality, dried over sodium sulfate, and evaporated under reduced pressure to yield hexyl 2-(6'-trifluoromethyl-2'-naphthyl)propionate.

By employing the 2-(6'-substituted-2'-naphthyl)acetic acid derivatives of Examples 1–16 in the above process, the corresponding hexyl 2-(6'-substituted-2'-naphthyl)acetate derivatives are obtained. For example hexyl 2-(6'-trifluoromethyl-2'-naphthyl)acetate,
hexyl 2-(6'-trifluoromethyl-2'-naphthyl)-3,3-difluoropropionate,
hexyl 2-(6'-trifluoromethyl-2'-naphthyl)acrylate,
hexyl 2-(6'-ethyl-2'-naphthyl)acetate,
hexyl 2-(6'-ethyl-2'-naphthyl)propionate,
hexyl 2-(6'-ethyl-2'-naphthyl)-3,3-difluoropropionate,
hexyl 2-(6'-ethyl-2'-naphthyl)acrylate,
hexyl 2-(6'-ethynyl-2'-naphthyl)acetate,
hexyl 2-(6'-ethynyl-2'-naphthyl)propionate,
hexyl 2-(6'-ethynyl-2'-naphthyl)-3,3-difluoropropionate,
hexyl 2-(6'-ethynyl-2'-naphthyl)acrylate,
hexyl 2-(6'-acetyl-2'-naphthyl)acetate,
hexyl 2-(6'-acetyl-2'-naphthyl)propionate,
hexyl 2-(6'-acetyl-2'-naphthyl)-3,3-difluoropropionate, and
hexyl 2-(6'-acetyl-2'-naphthyl)acrylate are prepared from the corresponding 2-(6'-substituted-2'-naphthyl)acetic acid derivatives.

EXAMPLE 32

A mixture of 21.4 g. of 2-(6'-methyl-2'-naphthyl)propionic acid, 1 ml. of dimethylformamide and 250 ml. of chloroform is refluxed with 12 g. of thionyl chloride for 4 hours. The mixture is then cooled and evaporated to dryness to yield 2-(6'-methyl-2'-naphthyl)propionyl chloride. The latter product is added to 250 ml. of carbon tetrachloride and 100 ml. of triethylamine. The resulting mixture is then treated with 50 ml. of tertiary butyl alcohol over a 1 hour period while maintaining the reaction temperature at 20° C. After the addition, the mixture is stirred for an additional 24 hours and diluted with 500 ml. of water. The aqueous mixture is extracted with methylene chloride; the extracts are combined, washed with water, dried over sodium sulfate and evaporated to yield tertiary butyl 2-(6'-methyl-2'-naphthyl)propionate.

EXAMPLE 33

Forty grams of powdered 2-(6'-chloro-2'-naphthyl)propionic acid are treated with 14 g. of phosphorus trichloride dropwise at room temperature under anhydrous conditions. After the addition of the phosphorus trichloride, the reaction mixture is heated to 100° C for 4 hours. The mixture is cooled, diluted with 200 ml. of carbon tetrachloride, filtered and evaporated to yield 2-(6'-chloro-2'-naphthyl)propionyl chloride.

The same product is obtained when 44.5 g. of the sodium salt of 2-(6'-chloro-2'-naphthyl)propionic acid is used in place of 2-(6'-chloro-2'-naphthyl)propionic acid and 15.3 g. of phosphorus oxychloride are used in place of phosphorus trichloride in the above process.

EXAMPLE 34

A mixture of 46 g. of 2-(6'-methyl-2'-naphthyl)propionic acid, 500 ml. of butanol, 600 ml. of tetrahydrofuran and 1 g. of p-toluenesulfonic acid are refluxed for 12 hours. The mixture is then cooled, diluted with 10 l. of water, and extracted with diethyl ether. The extracts are combined, washed with water and aqueous sodium bicarbonate, washed with water to neutrality and dried over sodium sulfate and evaporated to yield butyl 2-(6'-methyl-2'-naphthyl)propionate.

The same result is obtained when 5 ml. of concentrated sulfuric acid is used in place of p-toluenesulfonic acid in the above process.

By employing the 2-(6'-substituted-2'-naphthyl)acetic acid derivatives of Examples 1–16 in the above process, the corresponding butyl 2-(6'-substituted-2'-naphthyl)acetate derivatives are obtained. For example, butyl 2-(6'-methyl-2'-naphthyl)acetate,
butyl 2-(6'-methyl-2'-naphthyl)-3,3-difluoropropionate,
butyl 2-(6'-methyl-2'-naphthyl)acrylate,
butyl 2-(6'-difluoromethoxy-2'-naphthyl)acetate,
butyl 2-(6'-difluoromethoxy-2'-naphthyl)propionate,
butyl 2-(6'-difluoromethoxy-2'-naphthyl)-3,3-difluoropropionate,
butyl 2-(6'-difluoromethoxy-2'-naphthyl)acrylate,
butyl 2-(6'-chloro-2'-naphthyl)acetate,
butyl 2-(6'-chloro-2'-naphthyl)propionate,
butyl 2-(6'-chloro-2'-naphthyl)-3,3-difluoropropionate,
butyl 2-(6'-chloro-2'-naphthyl)acrylate,
butyl 2-(6'-methylthio-2'-naphthyl)acetate,
butyl 2-(6'-methylthio-2'-naphthyl)propionate,
butyl 2-(6'-methylthio-2'-naphthyl)-3,3-difluoropropionate, and
butyl 2-(6'-methylthio-2'-naphthyl)acrylate are prepared from the corresponding 2-(6'-substituted-2'-naphthyl)acetic acid derivatives.

EXAMPLE 35

The following alcohol reagents are employed in place of tertiary butyl alcohol in the process described in Example 32 to give the corresponding 2-(6'-substituted-2'-naphthyl)acetic acid ester derivatives: 2,3-dimethyl-2-hexanol, 2,5-dimethyl-2-hexanol, 2,3-dimethyl-3-pentanol, 3-ethyl-3-pentanol, 2-methyl-2-heptanol, 3-methyl-3-heptanol, 4-methyl-4-heptanol, 2-methyl-2-pentanol, 3-methyl-3-pentanol, 2-methyl-2-octanol, 4-methyl-4-octanol and 2-methyl-2-nonanol.

In a similar manner, the 2-(6'-substituted-2'-naphthyl)acetic acid derivatives of Examples 1–16 can be esterified by means of the above process to yield the corresponding tertiary butyl 2-(6'-substituted-2'-naphthyl)acetate derivatives.

EXAMPLE 36

The following alcohol reagents are employed in place of palmityl alcohol in Example 30 or in place of hexyl alcohol in Example 31 or in place of butyl alcohol in Example 32 to give the corresponding 2-(6'-substituted-2'-naphthyl)acetic acid ester derivatives: methanol, ethanol, propanol, 2-propanol, butanol, 2-butanol, pentanol, 2-pentanol, 3-pentanol, hexanol, 2-hexanol, 3-hexanol, heptanol, 2-heptanol, 3-heptanol, 4-heptanol, octanol, 2-octanol, 4-octanol, nonanol, 2-nonanol, 4-nonanol, 5-nonanol, decanol, 2-decanol, 3-decanol, 4-decanol, 5-decanol, undecanol, dodecanol, 2-dodecanol, tridecanol, 7-tridecanol, tetradecanol, pentadecanol, 2-pentadecanol, hexadecanol, heptadecanol, 2-heptadecanol, octadecanol, nonadecanol, 2-nonadecanol, eicosanol, heneicosanol, 2-methylpropanol, 3-methyl-2-butanol, 3-methyl-2-pentanol, 4-methyl-2-pentanol, 2-methyl-3-pentanol, 3-methyl-2-hexanol, 2-methyl-3-hexanol, 3-methyl-3-hexanol, 5-methyl-3-hexanol, 6-methyl-2-heptanol, 4-methyl-3-heptanol, 5-methyl-3-heptanol, 2-methyl-3-octanol, 3-methyl-4-octanol, 4-methyl-4-octanol, 2-methyl-3-nonanol, 2-methyl-4-nonanol, 3-methyl-4-nonanol, 4-methyl-4-nonanol, 2-ethyl-1-butanol, 4-ethyl-3-hexanol, 2-ethyl-1-hexanol, 5-ethyl-2-heptanol, 3,3-dimethyl-1-butanol, 3,3-dimethyl-2-butanol, 2,3-dimethyl-1-butanol, 2,2-dimethyl-3-butanol, 3,4-dimethyl-2-hexanol, 2,2-dimethyl-3-hexanol, 2,5-dimethyl-3-hexanol, 2,2-dimethyl-3-heptanol, 2,4-dimethyl-3-heptanol, benzyl alcohol, 2-phenylethanol, 3-phenylpropanol, 2-pentadecanol, 2-tetradecanol, cyclononanol, cyclopropanol, cyclobutanol, cyclodecanol, cycloheptanemethanol, cycloheptanol, cyclododecanol, cyclohexanol, 2-cyclopentylethanol, 2-cyclohexylethanol, cyclohexylmethanol, cyclooctanemethanol, cyclooctanol, cyclopentylmethanol, cyclopentanol, 3-cyclopentylpropanol, cyclopropylmethanol, 3-cyclohexylpropanol, cyclobutylmethanol, 2,3-dimethyl-2-butanol, 2,2-dimethyl-3-pentanol, 2,3-dimethyl-1-pentanol, 2-dedecanol, 2-hexadecanol, 2-methyl-1-butanol, 3-methyl-1-butanol, 3-methyl-2-hexanol, 3-methyl-1-pentanol, 4-methyl-1-pentanol, 2,2-dimethyl-1-propanol, 2-nonadecanol and the like.

EXAMPLE 37

A solution of 85 g. of diazomethane in 3 liters of diethyl ether is slowly added to a solution of 460 g. of d 2-(6'-methoxy-2'-naphthyl)propionic acid in 2 liters of diethyl ether over a one hour period with stirring. The resulting mixture is stirred for an additional hour and then flushed with nitrogen gas until clear. The solution is then evaporated to yield the methyl ester of d 2-(6'-methoxy-2'-naphthyl)propionic acid.

By employing 112 g. of diazoethane in place of diazomethane in the above process, the ethyl ester of d 2-(6'-methoxy-2'-naphthyl)propionic acid is obtained.

What is claimed is:
1. The isoamyl ester of d 2-(6'-methoxy-2'-naphthyl)propionic acid.
2. A compound selected from the group consisting of 2-(6'-methoxy-2'-naphthyl)propionic acid and the pharmaceutically acceptable salts thereof.
3. A compound selected from the group consisting of d 2-(6'-methoxy-2'-naphthyl)propionic acid and the pharmaceutically acceptable salts thereof.
4. A compound selected from the group consisting of 2-(6'-difluoromethoxy-2'-naphthyl)propionic acid and the pharmaceutically acceptable salts thereof.
5. A compound of claim 4 selected from the group consisting of dl-, d- and 1-2-(6'-difluoromethoxy-2'-naphthyl)propionic acid.
6. As a compound of claim 5, d 2-(6'-difluoromethoxy-2'-naphthyl)propionic acid.

7. The sodium salt of d 2-(6'-methoxy-2'-naphthyl)-propionic acid.

8. The sodium salt of 2-(6'-methoxy-2'-naphthyl)-propionic acid.

9. The pharmaceutically acceptable salts of 2-(6'-methoxy-2'-naphthyl)propionic acid.

10. The pharmaceutically acceptable salts of d 2-(6'-methoxy-2'-naphthyl)propionic acid.

11. 1 isoamyl 2-(6'-methoxy-2'-naphthyl)propionate.

* * * * *